US012231778B2

(12) United States Patent
Chono et al.

(10) Patent No.: US 12,231,778 B2
(45) Date of Patent: Feb. 18, 2025

(54) ILLUMINATION CONTROL APPARATUS, METHOD, SYSTEM, AND COMPUTER READABLE MEDIUM

(71) Applicant: NEC Corporation, Tokyo (JP)

(72) Inventors: Keiichi Chono, Tokyo (JP); Ryuichi Akashi, Tokyo (JP); Yuka Ogino, Tokyo (JP); Masato Tsukada, Tokyo (JP)

(73) Assignee: NEC CORPORATION, Tokyo (JP)

( * ) Notice: Subject to any disclaimer, the term of this patent is extended or adjusted under 35 U.S.C. 154(b) by 146 days.

(21) Appl. No.: 17/431,545

(22) PCT Filed: Feb. 12, 2020

(86) PCT No.: PCT/JP2020/005408
§ 371 (c)(1),
(2) Date: Aug. 17, 2021

(87) PCT Pub. No.: WO2020/170914
PCT Pub. Date: Aug. 27, 2020

(65) Prior Publication Data
US 2022/0141372 A1 May 5, 2022

(30) Foreign Application Priority Data
Feb. 18, 2019 (JP) .................. 2019-026940

(51) Int. Cl.
*H04N 23/74* (2023.01)
*G06V 10/141* (2022.01)
(Continued)

(52) U.S. Cl.
CPC .......... *H04N 23/74* (2023.01); *G06V 10/141* (2022.01); *G06V 40/19* (2022.01); *H04N 23/56* (2023.01)

(58) Field of Classification Search
CPC ...... H04N 23/74; H04N 23/56; G06V 10/141; G06V 40/19
See application file for complete search history.

(56) References Cited

U.S. PATENT DOCUMENTS 5,999,747 A * 12/1999 Imura .................. G03B 5/00
396/61
10,372,973 B2 * 8/2019 Davis .................. G06V 10/993
(Continued)

FOREIGN PATENT DOCUMENTS

| CN | 106295471 A | 1/2017 |
|---|---|---|
| JP | 2002-281275 A | 9/2002 |

(Continued)

OTHER PUBLICATIONS

International Search Report for PCT Application No. PCT/JP2020/005408, mailed on Apr. 14, 2020.
(Continued)

*Primary Examiner* — James T Boylan

(57) ABSTRACT

An illumination device emits light toward a moving subject. A controller controls light emitted from the illumination device so that the amount of light applied to the subject is adjusted to a specific amount or smaller. For example, when the illumination device emits light in a pulsed manner, the controller may control the amount of light applied to the subject by controlling at least one of the pulse width and the pulse intensity of the light. The controller may, for example, control the light emitted from the illumination device according to the distance between the illumination device and the subject.

10 Claims, 4 Drawing Sheets

(51) Int. Cl.
*G06V 40/19* (2022.01)
*H04N 23/56* (2023.01)

(56) References Cited

U.S. PATENT DOCUMENTS

| | | | | |
|---|---|---|---|---|
| 2005/0122420 | A1* | 6/2005 | Matsui | G03B 7/16 348/370 |
| 2009/0278658 | A1* | 11/2009 | Higashiyama | G06V 40/19 340/5.82 |
| 2016/0088241 | A1* | 3/2016 | Sung | G06V 40/19 382/117 |
| 2016/0094833 | A1* | 3/2016 | Rouh | G06V 40/197 348/48 |
| 2016/0198091 | A1* | 7/2016 | Edwards | G06F 1/3206 348/78 |
| 2017/0019577 | A1* | 1/2017 | Tan | H04N 23/611 |
| 2017/0061210 | A1* | 3/2017 | Ollila | H04N 1/00307 |
| 2017/0196451 | A1* | 7/2017 | Tian | G06V 20/64 |
| 2018/0173941 | A1* | 6/2018 | Shin | G06V 40/172 |
| 2018/0359424 | A1 | 12/2018 | Shibusawa et al. | |
| 2019/0012543 | A1* | 1/2019 | Zhou | G06V 40/193 |

FOREIGN PATENT DOCUMENTS

| | | | |
|---|---|---|---|
| JP | 2004-261515 A | 9/2004 | |
| JP | 2008-152097 A | 7/2008 | |
| JP | 2008-310480 A | 12/2008 | |
| WO | WO-2009016846 A1 * | 2/2009 | ......... G06K 9/00597 |

OTHER PUBLICATIONS

Masahiko Hosoya, "Identification System by Iris Recognition", Transactions of the Japanese Society for Medical and Biological Engineering 44(1), pp. 33-39, 2006.
John Daugman, "How Iris Recognition Works", pp. 1-10, [Online] <URL: https://www.cl.cam.ac.uk/~jgd1000/irisrecog.pdf>.
Extended European Search Report for EP Application No. 20759318.7 dated on Feb. 22, 2022.
JP Office Action for JP Application No. 2021-501892, mailed on Oct. 18, 2022 with English Translation.
CN Office Action for CN Application No. 202080022230.1, mailed on Jan. 12, 2024 with English Translation.
JP Office Action for JP Application No. 2023-074481, mailed on Oct. 1, 2024 with English Translation.

\* cited by examiner

ILLUMINATION CONTROL APPARATUS, METHOD, SYSTEM, AND COMPUTER READABLE MEDIUM

This application is a National Stage Entry of PCT/JP2020/005408 filed on Feb. 12, 2020, which claims priority from Japanese Patent Application 2019-026940 filed on Feb. 18, 2019, the contents of all of which are incorporated herein by reference, in their entirety.

TECHNICAL FIELD

The present disclosure relates to an illumination control apparatus, a method, a system, and a computer readable medium, and in particular to an illumination control apparatus, a method, a system, and a computer readable media that can be used for use for authentication using an iris(es).

BACKGROUND ART

Biometric authentication using an iris(es) has been known. In such biometric authentication, iris(es) of a subject is photographed by using an image pick-up apparatus, and feature values are extracted from the pattern of the photographed iris. In order to authenticate a subject, extracted feature values are compared with those registered in advance in a database, and a pass/fail is determined based on a score of matching therebetween. Further, in order to register a subject to be authenticated, extracted feature values are added in the database.

As described in Non-patent Literature 1, an iris, which is a donut-shaped tissue surrounding a pupil, has a very complex pattern, and is unique to each person. Further, in the photographing of an iris, near-infrared light is applied to eyes of a subject.

As described in Non-patent Literature 2, in the photographing of an iris(es), an image of the iris is taken with a resolution in which the radius of the iris is expressed by 100 to 140 pixels. Further, the wavelength of the near-infrared light applied to the eyes of the subject is in a range between 700 nm and 900 nm.

CITATION LIST

Non Patent Literature

Non-patent Literature 1: Hosoya, "Identification System by Iris Recognition", Japanese Society for Medical and Biological Engineering 44(1), pages 33-39, 2006

Non-patent Literature 2: Daugman, "How Iris Recognition Works," https://www.cl.cam.ac.uk/~jgd1000/iris-recog.pdf

SUMMARY OF INVENTION

Technical Problem

The diameter of an iris is about 1 cm. Therefore, when the radius of an iris is expressed by 100 pixels, the granularity becomes 50 μm. Since the pattern of an iris is microscopic as described above, it is difficult, under conditions that the distance between a subject and imaging means is large and the subject moves, to prevent strong light from being applied to the subject in close proximity to the illumination source while maintaining brightness necessary for photographing an iris pattern with quality with which the authentication and/or comparison thereof can be performed.

In view of the above-described circumstances, an object of the present disclosure is to provide an illumination control apparatus, a method, a system, and a computer readable medium capable of preventing strong light from being applied to a subject in close proximity to the illumination source.

Solution to Problem

In order to achieve the above-described object, in a first aspect, the present disclosure provides an illumination control system including: guiding means for guiding a subject; illumination means for illuminating the subject; image pick-up means for photographing the subject; and control means for controlling an amount of light applied to the subject to a specific amount or smaller.

As a second aspect, the present disclosure provides an illumination control apparatus including control means for controlling light emitted from illumination means so that an amount of light applied from the illumination means to a moving subject is adjusted to a specific amount or smaller, the illumination means being configured to emit the light to the moving subject.

As a third aspect, the present disclosure provides an illumination control method for controlling light emitted from illumination means so that an amount of light applied from the illumination means to a moving subject is adjusted to a specific amount or smaller, the illumination means being configured to emit the light to the moving subject.

As a fourth aspect, the present disclosure provides a computer readable medium storing a program for causing a computer to perform a process for controlling light emitted from illumination means so that an amount of light applied from the illumination means to a moving subject is adjusted to a specific amount or smaller, the illumination means being configured to emit the light to the moving subject.

Advantageous Effects of Invention

An illumination control apparatus, a method, a system, and a computer readable medium according to the present disclosure can prevent strong light from being applied to a subject in close proximity to the illumination source.

DESCRIPTION OF EMBODIMENTS

Figure 1:
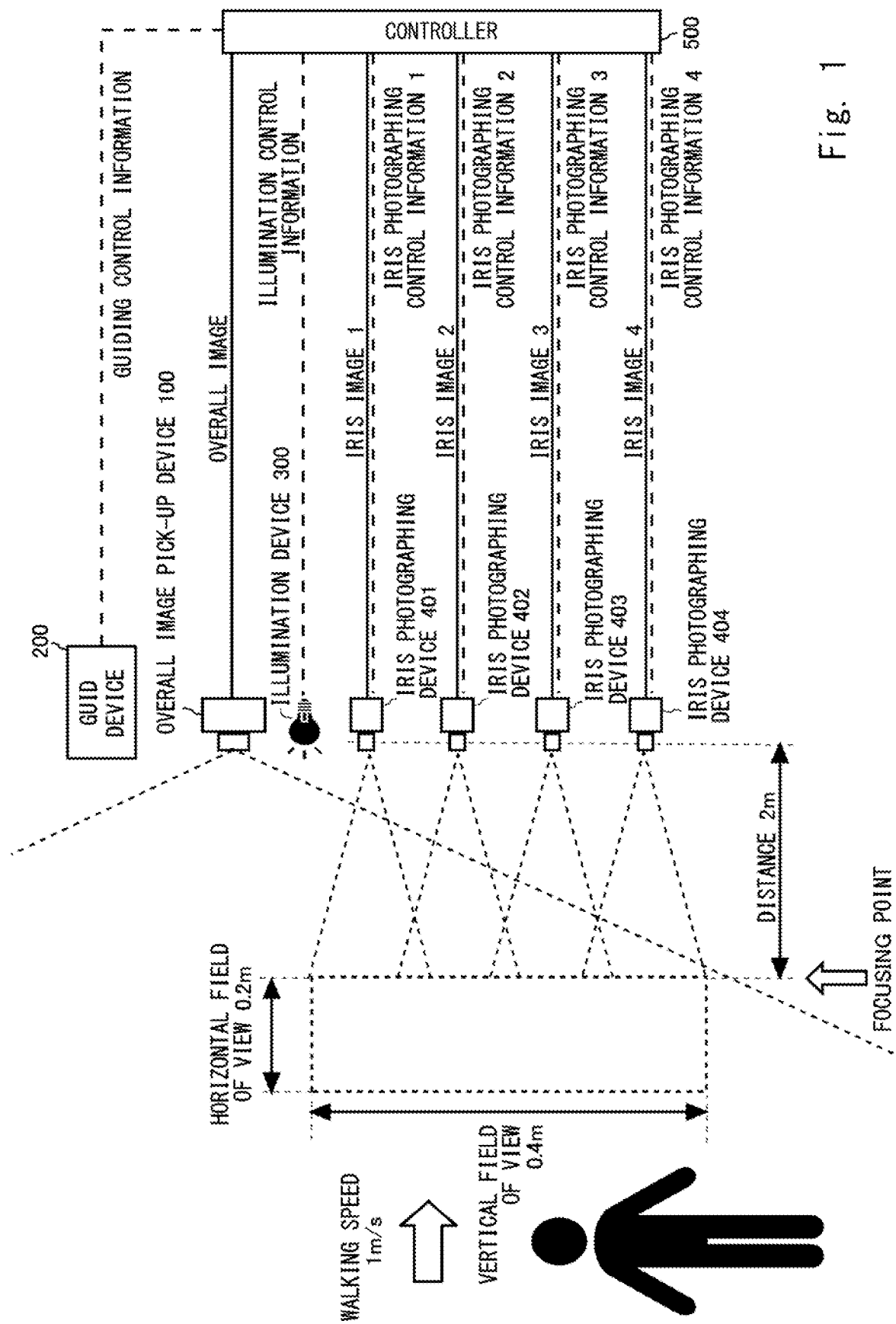
FIG. 1 is a block diagram showing an image processing system including an illumination control system according to an example embodiment of the present disclosure.

Prior to giving the description of an example embodiment according to the present disclosure, a problem thereof is quantitively described. As an example, the below-shown conditions, which are assumed as operational conditions for Automated Border Control systems (ABC systems) and the like, will be described hereinafter. It is assumed that a distance between a subject and image pick-up means (the distance between a subject and a gate) is 2 m, and a horizontal field of view, i.e., a range in the horizontal direction in which both eyes of one subject can be covered, is 0.2 m. Further, a vertical field of view, i.e., a range in the vertical direction in which the eyes of a wide range of subjects from a tall subject, typically a male person, to a short subject, typically a female person, can be covered, is 0.4 m. Further, it is assumed that the walking speed (the moving speed) of the subject relative to the gate is equal to the average of slow walking speeds of adult people, e.g., is 1 m/s.

When a position 2 m away from the image pick-up means is defined as a position where irises of a subject walking from a place more distant than the aforementioned position are brought into focus and photographed (i.e., is used as a focusing point), it is necessary to apply, from illumination means to the subject, light having such a level that an iris pattern can be photographed with quality with which the authentication and/or comparison thereof can be performed. For example, it is assumed that the amount of light applied to the subject at the position 2 m away, i.e., the subject at the focusing point, is 5 mW/cm². The amount of light applied to the subject attenuates in proportion to the square of the distance between the subject and the illumination source, so that the amount of light applied to the subject at 1 m away becomes 20 mW/cm². The fact that strong light is applied to the subject in close proximity to the illumination source is undesirable in terms of safety.

On the other hand, when the amount of light applied to the subject at a position 1 m away is 5 mW/cm², the amount of light applied to the subject at a position 2 m away is 1.25 mW/cm². In the photographing of an iris pattern, in some cases, for example, the photographing is performed with a short exposure time in order to avoid blurring of the iris pattern due to the movement of a moving subject. Further, in some cases, a large aperture value is used in an image pick-up apparatus so that the depth of field with which the iris pattern of a moving subject is clearly photographed is increased. In such cases, a large amount of light is lost in the optical system of the image pick-up apparatus. Because of the above-described circumstances, there is a possibility that when the amount of light is reduced, it may be impossible to photograph the iris pattern with quality with which the authentication and/or comparison thereof can be performed.

Since the pattern of an iris is microscopic, it is difficult, under conditions that the distance between a subject and an illumination source is large and the subject may move toward the illumination source, to prevent strong light from being applied to the subject in close proximity to the illumination source while maintaining brightness necessary for photographing an iris pattern with quality with which the authentication and/or comparison thereof can be performed.

Example embodiments according to the present disclosure will be described hereinafter with reference to the drawings. FIG. 1 shows an image processing system including an illumination control system according to an example embodiment of the present disclosure. The image processing system includes an overall imaging device 100, a guiding device 200, an illumination device 300, iris image pick-up devices 401 to 404, and a controller 500. Note that although the number of iris image pick-up devices is four in FIG. 1, the number of iris image pick-up devices is not limited to any particular number. The number of iris image pick-up devices can be set as appropriate according to the field of view to be covered and the resolutions of available iris image pick-up devices.

The overall imaging device (overall image pick-up means) 100 photographs a subject with a wide field of view that is wide enough to cover a whole range of subjects from a tall subject to a short subject. The overall imaging device 100 may have a resolution in which a subject can be authenticated by his/her face.

The controller (control means) 500 monitors an overall image supplied from the overall imaging device 100, and controls the guiding device (guiding means) 200, the illumination device (illumination means) 300, and the plurality of iris image pick-up devices (image pick-up means) 401 to 404. The functions of the controller 500 can be implemented by hardware or by a computer program(s). The controller 500 determines a start of biometric authentication for the subject based on his/her overall image supplied from the overall imaging device 100, or based on an external input.

The control performed by the controller 500 includes guiding control, illumination control, and iris image pick-up control. In the guiding control, the controller 500 supplies guiding control information for guiding the subject to the guiding device 200. The guiding device 200 guides the subject based on the guiding control information. The guiding device 200 includes, for example, a display and/or a speaker(s). For example, the guiding device 200 presents an image(s) and a sound(s) for indicating the start of biometric authentication through the display and/or the speaker, respectively. Further, the guiding device 200 presents images and sounds for inducing the subject to turn his/her eyes to the iris image pick-up devices through the display and/or the speaker, respectively.

In the illumination control, the controller 500 supplies, to the illumination device 300, illumination control information for applying illumination light to the subject. The illumination device 300 applies light (e.g., near-infrared light) to the subject based on the illumination control information. The illumination device 300 includes LEDs (Light Emitting Diodes) as a light source, and a synchronization signal generator. The amount of light applied from the illumination device 300 to the subject is determined by the value of the current supplied to the LEDs, the lighting time of the LEDs, and the lighting cycle thereof, and the illumination control information includes the numerical values thereof. When the LEDs are not continuously kept in the on-state, the lighting cycle of the LEDs is synchronized with the frame rates of the plurality of iris image pick-up devices 401 to 404.

In the iris image pick-up control, the controller 500 determines, based on the overall image supplied from the overall imaging device 100, one of the plurality of iris image pick-up devices 401 to 404 that can suitably photograph an area of the subject including his/her eyes. Further, the controller 500 determines the vertical position of a region of interest that is read out at a high speed in the determined iris image pick-up device.

Figure 2:
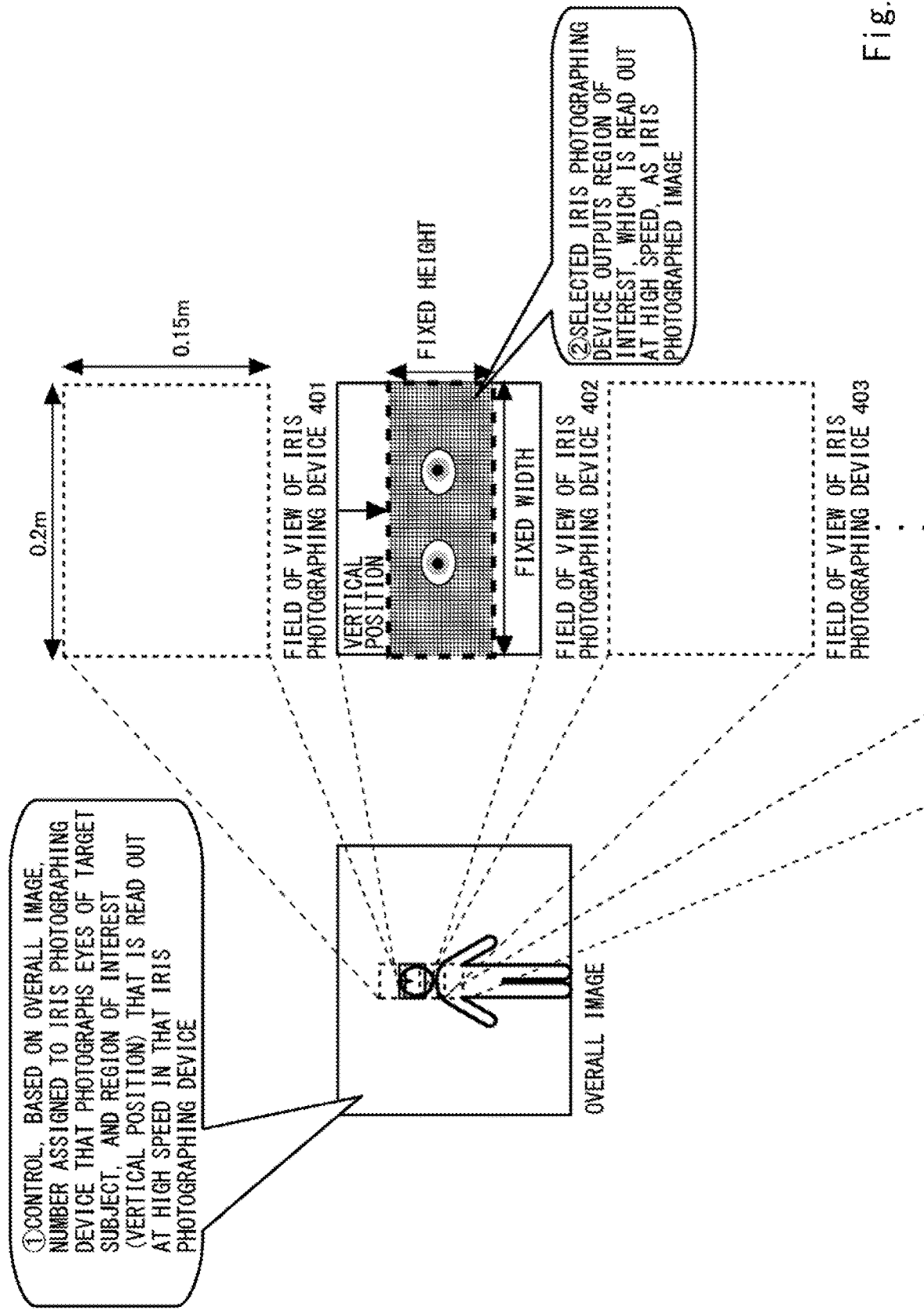
FIG. 2 shows a state of iris image pick-up control.

FIG. 2 shows a state of the iris image pick-up control. Details of the iris image pick-up control will be described with reference to FIG. 2. In this example, it is assumed that a general-purpose camera having 12 M pixels (4,000 horizontal pixels and 3,000 vertical pixels) and a frame rate of 60 fps is used for each of the iris image pick-up devices 401 to 404. Such cameras have been becoming widespread as industrial cameras. In the case where the photographing is performed with a granularity of 50 μm, with which a subject can be authenticated by his/her iris, the horizontal and vertical fields of view of each of the iris image pick-up devices are 0.2 m (4,000×50 [μm]=0.2 [m]) and 0.15 m (3,000×50 [μm]=0.15 [m]), respectively.

The plurality of iris image pick-up devices 401 to 404 are arranged so that they are stacked on top of each other in the vertical direction. Note that the plurality of iris image pick-up devices 401 to 404 are arranged so that the image areas of iris image pick-up devices adjacent to each other partially overlap each other. For example, the iris image pick-up devices 401 to 404 are arranged so that the image areas of iris image pick-up devices adjacent to each other overlap each other by 2.5 cm. In such a case, at the focusing point 2 m away from the four iris image pick-up devices, they can secure a field of view of 0.2 m in the horizontal direction and 0.45 m ((0.15−0.025)+(0.15−0.025−0.025)+(0.15−0.025−0.025)+(0.15−0.025) m) in the vertical direction. That is, it is possible to secure the required field of view of 0.2 m in the horizontal direction and 0.4 m in the vertical direction. Note that it can be understood, by the drawings and the above description, that the iris image pick-up devices have the same fields of view as each other and are placed in positions different from each other.

In the case where the frame rate of each of the iris image pick-up devices is 60 fps, they cannot meet the required frame rate of 100 fps when they are used as they are. Note that an industrial camera or the like has a region-of-interest mode. In the region-of-interest mode, only a partial area that is defined as a region of interest is read out instead of reading out the entire area of the screen. It is possible to increase the frame rate by using such a region-of-interest mode.

The controller 500 sets a region of interest in any given iris image pick-up device and reads out the image in the region of interest from that iris image pick-up device. In the example shown in FIG. 2, a partial area of 4,000 pixels in the horizontal direction and 1,500 pixels in the vertical direction, which corresponds to a half of the entire area of the screen, is defined as the region of interest. In this case, since the number of pixels in each frame is a half of the number of pixels in the entire area, it is possible to increase the frame rate to 120 fps, which is twice the frame rate of 60 fps in the case where the entire area of the screen is read out. However, the horizontal and vertical fields of view of the partial area become 0.2 m and 0.75 m, respectively. Note that both eyes of a human being are aligned in the horizontal direction. Therefore, in the region-of-interest, it is preferred to reduce the number of pixels in the vertical direction, instead of reducing that in the horizontal direction, so that both eyes can be photographed.

Under the condition that the area of eyes is not photographed in the above-described range where the image areas of iris image pick-up devices adjacent to each other overlap each other, the iris image pick-up device that photographs the area of eyes is only one of the four iris image pick-up devices 401 to 404. Further, the condition under which the image can be read out at the frame rate of 120 fps is a partial area in that iris image pick-up device. The controller 500 infers one of the iris image pick-up devices 401 to 404 that can suitably photograph the area of eyes, and estimates the vertical position of the region of interest in which the image is read out at a high speed in that iris image pick-up device.

The above-described inference/estimation can be carried out by a method described below. The overall imaging device 100 has a resolution in which a subject can be authenticated by his/her face, and the controller 500 derives the positions of the eyes of the subject in the overall image taken by the overall imaging device 100. The controller 500 derives the iris image pick-up device corresponding to the positions of the eyes of the subject in the overall image and the positions of the eyes present in that imaging device by using camera parameters and the positional relation of the overall imaging device 100 and each of the iris image pick-up devices. By using the region-of-interest mode, it is possible, by using a general-purpose camera, to achieve a field of view wider than 0.2 m in the horizontal direction and 0.4 m in the vertical direction, and a temporal resolution higher than 100 fps.

Note that when the vertical position is changed in the above-described region-of-interest mode, a delay occurs before the start of the photographing. Therefore, in the above-described inference/estimation, an image that is obtained by photographing the subject at a position that is more distant than the position 2 meters away, i.e., more distant than the focusing point of the iris image pick-up device, e.g., by photographing the subject at a position 3 meters away may be used. The resolution in which a subject present at a position 3 meters away can be authenticated by his/her face can be achieved by a camera having about 2 M pixels, so that cameras having specifications lower than those of the iris image pick-up cameras can be used for the overall imaging device 100.

The controller 500 supplies iris image pick-up information to each of the iris image pick-up devices 401 to 404 based on the above-described iris image pick-up control. The controller 500 supplies iris image pick-up information including the vertical position of the region of interest to the iris image pick-up device that photographs the area of the eyes of the subject. The controller 500 may supply optional iris image pick-up information to the other iris image pick-up devices. The controller 500 may supply iris image pick-up information including information about the stop of the supply of the iris image to the other iris image pick-up devices, for example, in order to reduce the total amount of the data of the iris image.

Each of the iris image pick-up devices 401 to 404 supplies the iris image to the controller 500 based on the iris image pick-up information supplied from the controller 500. Note that each of the iris image pick-up devices 401 to 404 outputs the image in the region of interest that is set by the controller 500 by using the iris image pick-up information (i.e., the iris image) to the controller 500. Each of the iris image pick-up devices 401 to 404 may lossy-compress the iris image in the region of interest and output the compressed iris image to the controller 500. For example, each of the iris image pick-up devices 401 to 404 compresses the iris image in the region of interest by using quantization (pixel-by-pixel compression), predictive coding and quantization (compression on a basis of a plurality of pairs of pixels), or a combination of transform coding and quantization (compression on a basis of a plurality of pairs of pixels). The controller 500 performs the authentication and the registration described in the background section by using the iris images supplied from the iris image pick-up devices 401 to 404. The controller 500 returns to the next process when there is a next subject or when the authentication or the registration has failed.

Note that, in this example embodiment, the controller 500 controls the light emitted from the illumination device 300 so that the amount of light applied from the illumination device 300 to a moving subject is adjusted to a specific amount or smaller. The illumination device 300 emits light, for example, in a pulsed manner. In such a case, the controller 500 controls the amount of light applied to the subject by controlling at least one of the pulse width and pulse intensity of the light emitted from the illumination device 300. The pulse width corresponds to the lighting time of the LEDs or the like, and the pulse intensity corresponds to the current supplied to the LEDs. The controller 500, for example, controls the light emitted from the illumination device 300 according to the distance between the illumination device 300 and the subject. The controller 500 calculates the amount of light emitted from the illumination device 300 by using, for example, a predetermined calculation formula which is a function of the distance. Alternatively, the controller 500 may determine the amount of light emitted from the illumination device 300 according to the distance by using a table in which a relation between distances and amounts of light emitted from the illumination device 300 is defined.

In this example embodiment, the illumination control performed by the controller 500 includes first illumination control and second illumination control. The controller 500 performs the first illumination control when the position of the subject is near the focusing point of the iris image pick-up device, or is more distant than the focusing point thereof. The controller 500 performs the second illumination control after the subject has passed through the focusing point of the iris image pick-up device. In this example embodiment, the controller 500 also functions as an illumination control apparatus that carries out an illumination control method. Note that although an example in which the iris image pick-up devices 401 to 404 are used as the image pick-up means has been described in this example embodiment, any apparatuses or the like can be used as the image pick-up means as long as they can photograph a subject. That is, the image pick-up means is not limited to the iris image pick-up devices 401 to 404.

In the first illumination control, the controller 500 makes the illumination device 300 emit light having such an amount of light that light which is bright enough to enable the iris pattern of the subject to be photographed at the focusing point of the iris image pick-up device with quality with which the authentication and/or comparison thereof can be performed is applied to the subject. In the first illumination control, for example, the controller 500 adjusts the amount of light emitted from the illumination device 300 to the controllably-possible maximum value. It is assumed that the amount of light applied to the subject at the time of the first illumination control is, for example, an amount of light that satisfies predetermined safety standards.

In the second illumination control, the controller 500 controls the amount of light emitted from the illumination device 300 through the illumination control information so that the amount of light applied to the subject is adjusted to a specific amount or smaller. In the second illumination control, the controller 500 reduces the amount of light emitted from the illumination device 300 from the controllably-possible maximum value. For example, in the second illumination control, the controller 500 reduces the value of the current supplied to the LEDs of the illumination device 300 as compared to that in the first illumination control, and thereby lowers the light-emitting intensity of the illumination device 300. Alternatively, in the second illumination control, the controller 500 shortens the lighting time (the light-emitting time) of the LEDs of the illumination device 300 as compared to that in the first illumination control. In the second illumination control, the controller 500 may reduce the value of the current supplied to the LEDs of the illumination device 300 and shorten the lighting time of the LEDs as compared to those in the first illumination control. The controller 500 may turn off the illumination device 300 in the second illumination control. That is, the application of the light to the subject may be stopped.

Note that the fact that the subject passes through the focusing point of the iris image pick-up device means a fact that the subject moves to the near side of the focusing point (i.e., to the side of the focusing point on which the image pick-up device and the like are located), and moves close to the illumination device 300 and the iris image pick-up devices 401 to 404. In the case where the process for the authentication or registration is performed at a sufficiently high speed, the controller 500 may regard the time at which the authentication or registration is completed as the time at which the subject has passed through the focusing point, and determine that the subject has already passed through the focusing point. When the controller 500 determines that the subject has already passed through the focusing point, it may switch the illumination control from the first illumination control to the second illumination control.

The method by which the controller 500 determines whether or not the subject has passed through the focusing point is not limited to any particular methods. For example, the controller 500 may determine whether or not the subject has already passed through the focusing point by using information about the position of the subject obtained by using the overall imaging device 100 having a distance-measurement function such as a Time of Flight (ToF) function. Alternatively, the controller 500 may monitor the brightness of the iris image supplied from the iris image pick-up device and determine whether or not the subject has already passed through the focusing point based on the brightness of the iris image. The brightness of the iris image changes depending on the amount of light applied to the subject. The closer the subject is to the illumination device 300, the brighter the iris image becomes. Therefore, it is possible to determine the position of the subject with some accuracy based on the brightness of the iris image.

Figure 3:
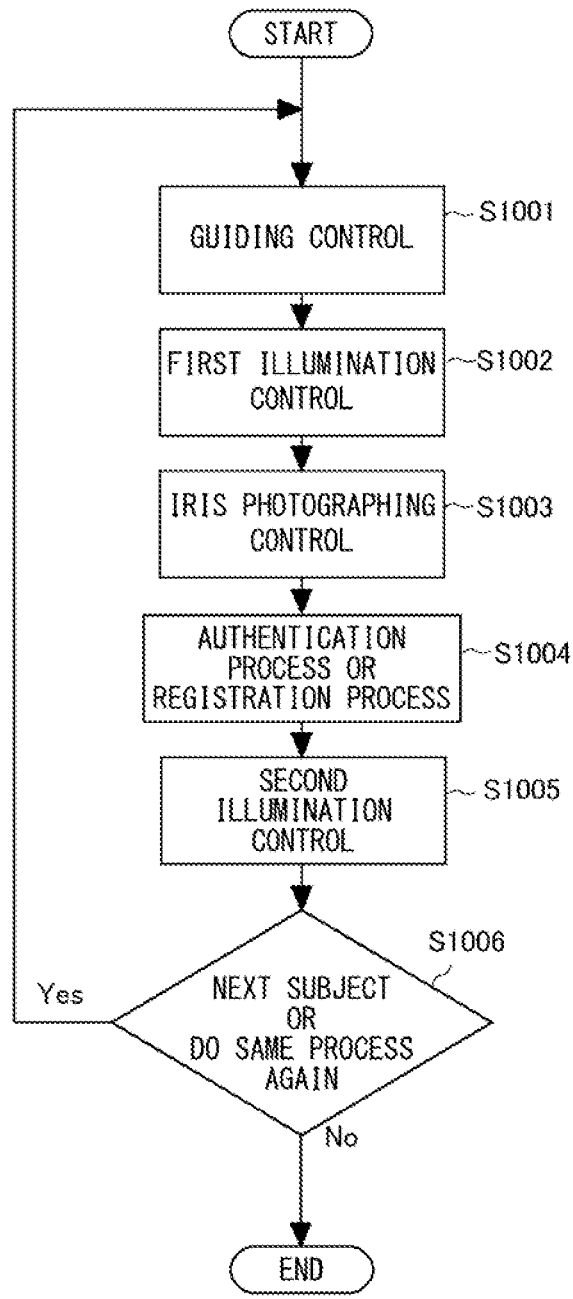
FIG. 3 is a flowchart showing an operational procedure in an image processing system.

Next, an operational procedure will be described. FIG. 3 shows an operational procedure in the image processing system. The controller 500 performs guiding control and thereby guides a subject by using the guiding device 200 (step S1001). The controller 500 performs the first illumination control and thereby applies infrared light to the subject by using the illumination device 300 (step S1002). The controller 500 performs the above-described iris image pick-up control and thereby acquires an image(s) of an iris(es) (an iris image(s)) by using the plurality of iris image pick-up devices 401 to 404 (step S1003). The iris image(s) acquired in the step S1003 is used for the authentication or registration of the iris. In the step S1003, the controller 500 does not need to obtain the iris image from each of the iris image pick-up devices 401 to 404 for a given subject as described above. The controller 500 obtains the iris image from the iris image pick-up device that has photographed the area of the eyes of the subject.

The controller 500 performs iris-based authentication by using the iris image acquired in the step S1003, or registers the iris image (step S1004). The controller 500 performs the second illumination control and thereby reduces the amount of light applied to the subject from the illumination device 300 to a specific amount or smaller (step S1005). Note that the timing at which the second illumination control is performed is not limited to the timing after the authentication or registration. For example, in the case where the process for the authentication or registration is not performed at a sufficiently high speed, the step S1005 may be performed before the step S1004, and the second illumination control may be performed before the authentication or registration is completed.

The controller 500 determines whether or not there is a next subject, or whether or not re-authentication or re-registration should be performed (step S1006). When it is determined that there is a next subject, or re-authentication or re-registration should be performed, the process returns to the step S1001 and the process is performed starting from the guiding control.

Note that when the overall imaging device 100 according to this example embodiment has a resolution in which a subject can be authenticated by his/her face, and holds feature values for authenticating the subject by his/her face in a database but does not hold feature values for authenticating the subject by his/her iris in the database, the apparatus according to the present disclosure can also be used for a use in which the apparatus identifies a subject based on face-based authentication and registers extracted feature values of the iris(es) of the subject in the database. Further, the apparatus according to the present disclosure can also be used for a use in which the apparatus estimates information about the height of a subject based on information about the positions of the eyes obtained by the iris image pick-up control, or information about the positions of the eyes that is obtained when an iris image obtained by the iris image pick-up device is authenticated or registered, and registers the estimated information in the database. Further, the apparatus according to the present disclosure can be used, by using the estimated information about height, to determine or calibrate the vertical position of one of iris image pick-up devices that can suitably photograph the area of eyes and the region of interest in which the image is read out at a high speed in that iris image pick-up device.

In this example embodiment, the controller 500 makes the illumination device 300 emit light having such an amount of light that light which is bright enough to enable the iris pattern of the subject to be photographed at the focusing point of the iris image pick-up device with quality with which the authentication and/or comparison thereof can be performed is applied to the subject. After the subject has passed through the focusing point, the controller 500 controls the amount of light emitted from the illumination device 300 so that the amount of light applied to the subject is adjusted to a specific amount or smaller. In this way, it is possible, under conditions that the distance between a subject and image pick-up means is large and the subject may move, to prevent strong light from being applied to the subject in close proximity to the illumination source while maintaining brightness necessary for photographing an iris pattern with quality with which the authentication and/or comparison thereof can be performed.

Note that although an example in which a partial area of 4,000 pixels in the horizontal direction and 1,500 pixels in the vertical direction is defined as the region of interest in FIG. 2, the present disclosure is not limited to this example. The shape of the region of interest is not limited to the rectangle, and the number of region of interest s is not limited to one. The controller 500 may, for example, derive the positions of the right eye and left eye of the subject from the overall image (the overlooked image) taken by the overall imaging device 100, and set a region of interest corresponding to the position of the right eye and a region of interest corresponding to the position of the left eye in the iris image pick-up device. In such a case, the iris image pick-up device supplies iris images of the right and left eyes to the controller 500. The shape of the region of interest may be rectangular or may be elliptic. The controller 500 may derive the positions of the right and left eyes of the subject based on the iris image taken by the iris image pick-up device instead of based on the overlooked image. For example, the controller 500 may temporarily define the partial area shown in FIG. 2 as the region of interest, and derive the positions of the right and left eyes from the images in the region of interest. In such a case, the controller 500 may set, based on the derived positions of the right and left eyes, each of a partial area corresponding to the position of the right eye and a partial area corresponding to the position of the left eye as a region of interest in the iris image pick-up device.

Figure 4:
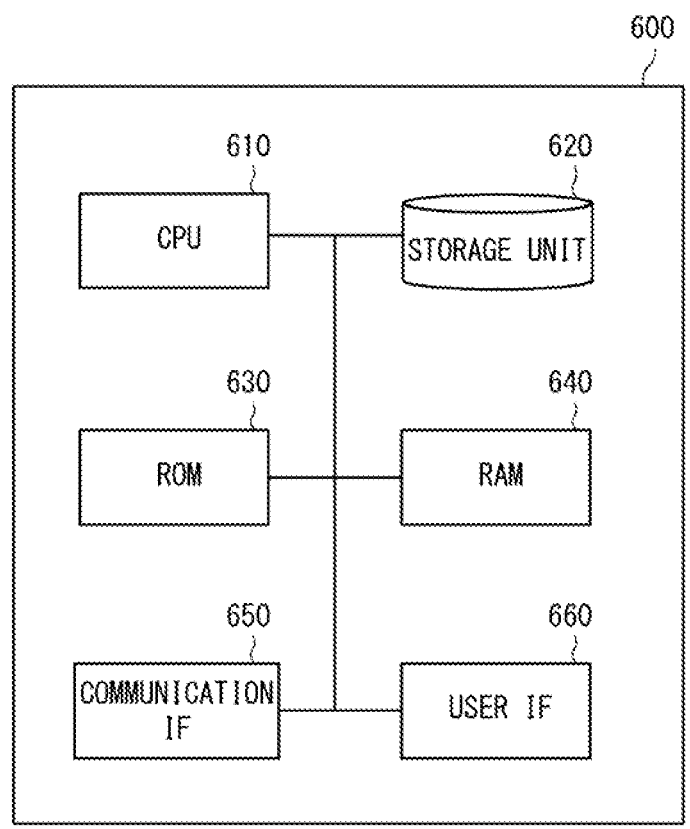
FIG. 4 is a block diagram showing an example of a configuration of a computer apparatus.

In the above-described example embodiment, the controller 500 can be formed as a computer apparatus. FIG. 4 shows an example of a configuration of an information processing apparatus (a computer apparatus) that can be used for the controller 500. An information processing apparatus 600 includes a control unit (CPU: Central Processing Unit) 610, a storage unit 620, a ROM (Read Only Memory) 630, a RAM (Random Access Memory) 640, a communication interface (IF: Interface) 650, and a user interface 660.

The communication interface 650 is an interface for connecting the information processing apparatus 600 to a communication network through wired communication means, wireless communication means, or the like. The user interface 660 includes, for example, a display unit such as a display. Further, the user interface 660 includes an input unit such as a keyboard, a mouse, and a touch panel.

The storage unit 620 is an auxiliary storage device that can hold various types of data. The storage unit 620 does not necessarily have to be a part of the information processing unit 600, and may be an external storage device or a cloud storage connected to the information processing unit 600 through a network. The ROM 630 is a non-volatile storage device. For example, a semiconductor storage device such as a flash memory having relatively small capacity is used for the ROM 630. Programs executed by the CPU 610 can be stored in the storage unit 620 or the ROM 630.

The aforementioned program can be stored and provided to the information processing apparatus 600 by using any type of non-transitory computer readable media. Non-transitory computer readable media include any type of tangible storage media. Examples of non-transitory computer readable media include magnetic storage media such as floppy disks, magnetic tapes, and hard disk drives, optical magnetic storage media such as magneto-optical disks, optical disk media such as CD (Compact Disc) and DVD (Digital Versatile Disk), and semiconductor memories such as mask ROM, PROM (Programmable ROM), EPROM (Erasable PROM), flash ROM, and RAM. Further, the program may be provided to a computer using any type of transitory computer readable media. Examples of transitory computer readable media include electric signals, optical signals, and electromagnetic waves. Transitory computer readable media can provide the program to a computer via a wired communication line such as electric wires and optical fibers or a radio communication line.

The RAM 640 is a volatile storage device. As the RAM 640, various types of semiconductor memory apparatuses such as a DRAM (Dynamic Random Access Memory) or an SRAM (Static Random Access Memory) can be used. The RAM 640 can be used as an internal buffer for temporarily storing data and the like. The CPU 610 expands (i.e., loads) a program stored in the storage unit 620 or the ROM 630 in the RAM 640, and executes the expanded (i.e., loaded) program. By executing the program, the CPU 610 performs various types of control including, for example, guiding control, illumination control, and iris image pick-up control.

Although example embodiments according to the present disclosure have been described above in detail, the present disclosure is not limited to the above-described example embodiments, and the present disclosure also includes those that are obtained by making changes or modifications to the above-described example embodiments without departing from the spirit of the present disclosure.

This application is based upon and claims the benefit of priority from Japanese patent application No. 2019-026940, filed on Feb. 18, 2019, the disclosure of which is incorporated herein in its entirety by reference.

REFERENCE SIGNS LIST

100 OVERALL IMAGING DEVICE
200 GUIDING DEVICE
300 ILLUMINATION DEVICE
401-404 IRIS IMAGE PICK-UP DEVICE
500 CONTROLLER
600 INFORMATION PROCESSING APPARATUS

The invention claimed is:

1. An illumination control system comprising:
a light source configured to illuminate a subject with a first amount of light;
an iris camera configured to photograph an iris image including a portion of an iris of the subject, on which basis the subject is authenticated;
one or more processors; and
a memory storing program code executable by the one or more processors to control light emitted from the light source, wherein
the one or more processors determine whether or not the subject has passed through a focusing point based on a brightness of the iris image photographed when the subject is illuminated with the first amount of the light, and control, when having determined that the subject has passed through the focusing point, the light source to illuminate the subject with a second amount of the light smaller than the first amount of the light.

2. The illumination control system according to claim 1, wherein
the light source emits the light in a pulsed manner, and
the one or more processors control an amount of the light applied to the subject by controlling at least one of a pulse width or a pulse intensity of the light.

3. An illumination control apparatus comprising:
one or more processors; and
a memory storing program code executable by the one or more processors to control light emitted from a light source configured to illuminate a subject with a first amount of the light, the subject being authenticated by iris authentication based on an iris image including a portion of an iris of the subject photographed by an iris camera, wherein
the one or more processors determine whether or not the subject has passed through a focusing point based on a brightness of the iris image photographed when the subject is illuminated with the first amount of the light, and control, when having determined that the subject has passed through the focusing point, the light source to illuminate the subject with a second amount of the light smaller than the first amount of the light.

4. The illumination control apparatus according to claim 3, wherein
the light source emits the light in a pulsed manner, and
the one or more processors control an amount of the light applied to the subject by controlling at least one of a pulse width or a pulse intensity of the light.

5. The illumination control apparatus according to claim 3, wherein when the subject is at the focusing position, or is more distant than the focusing position point thereof, the one or more processors perform first illumination control in which the light emitted from the light source has a brightness with which an iris image having a predetermined quality is taken at the focusing position by the iris camera is applied to the subject.

6. The illumination control apparatus according to claim 5, wherein when the subject is located closer to the light source than to the focusing position, the one or more processors perform second lighting control in which the light has either or both of a lower light-emitting intensity and a shorter light-emitting time.

7. An illumination control method comprising:
controlling light emitted from a light source configured to illuminate a subject with a first amount of the light, the subject being authenticated by iris authentication based on an iris image including a portion of an iris of the subject photographed by an iris camera;
determining whether or not the subject has passed through a focusing point based on a brightness of the iris image photographed when the subject is illuminated with the first amount of the light; and
controlling, when having determined that the subject has passed through the focusing point, the light source to illuminate the subject with a second amount of the light which is smaller than the first amount of the light.

8. The illumination control apparatus according to claim 3, wherein a lighting cycle of the light source is synchronized with a frame rate of the iris camera.

9. The illumination control apparatus according claim 3, wherein the one or more processors estimate height information of the subject using information about positions of eyes of the subject obtained from an eye image, and use the estimated height information to select the iris camera for photographing from among a plurality of the iris cameras.

10. The illumination control apparatus according to claim 3, wherein the one or more processors perform authentication or registration using the iris image of the subject illuminated with the first amount of the light, and control, after the authentication or registration has been performed, the light source to illuminate the subject with the second amount of the light.

* * * * *